United States Patent [19]

Requieme et al.

[11] Patent Number: 5,900,514

[45] Date of Patent: May 4, 1999

[54] SYNTHESIS OF DIFLUOROMETHANE

[75] Inventors: Benoit Requieme, Charly; Eric Lacroix, Amberieux D'Azergues; Andre Lantz, Vernaison, all of France

[73] Assignee: Elf Atochem S.A., Paris La Defense, France

[21] Appl. No.: 08/663,977

[22] Filed: Jun. 14, 1996

[30] Foreign Application Priority Data

Jun. 27, 1995 [FR] France .................................... 95 07705

[51] Int. Cl.$^6$ ..................................................... C07C 19/08
[52] U.S. Cl. ........................... 570/134; 570/169; 570/168
[58] Field of Search .................................... 570/134, 169, 570/168

[56] References Cited

U.S. PATENT DOCUMENTS

| | | |
|---|---|---|
| 2,745,886 | 5/1956 | Ruh . |
| 3,644,545 | 2/1972 | Buckman . |
| 5,051,537 | 9/1991 | Manzer . |
| 5,494,876 | 2/1996 | Tsjui .......................................... 570/168 |
| 5,523,500 | 6/1996 | Cheminal .................................. 570/169 |

FOREIGN PATENT DOCUMENTS

| | | |
|---|---|---|
| 2088460 | 7/1993 | Canada . |
| 328127 | 8/1989 | European Pat. Off. . |
| 554165 | 4/1993 | European Pat. Off. . |
| 51/082206 | 7/1976 | Japan . |
| WO 97/11043 | 3/1997 | WIPO . |

OTHER PUBLICATIONS

French Search Report dated Feb. 21, 1996.

*Primary Examiner*—Gary Geist
*Assistant Examiner*—Jean F. Vollano
*Attorney, Agent, or Firm*—Bell, Bond & Lloyd

[57] ABSTRACT

The invention relates to the manufacture of difluoromethane by catalytic gas-phase fluorination of methylene chloride.

The operation is carried out in the presence of oxygen at a temperature of between 330 and 450° C. and with a bulk or supported chromium catalyst.

10 Claims, No Drawings

SYNTHESIS OF DIFLUOROMETHANE

FIELD OF THE INVENTION

The present invention relates to the field of fluorohydrocarbons and more particularly its subject is the manufacture of difluoromethane (F32) by fluorination of methylene chloride.

Difluoromethane, known under the designation of F32, presents no danger to the ozone layer. It is therefore particularly advantageous for the replacement of CFCs. As a mixture with other hydrofluoroalkanes such as 1,1,1-trifluoroethane (F143a), 1,1,1,2-tetrafluoroethane (F134a) or pentafluoroethane (F125) it is intended especially to replace F22 (chlorodifluoromethane) and F502 (azeotropic mixture of F22 and of chloropentafluoroethane) in the field of refrigeration, of conditioned air and in other applications.

BACKGROUND OF THE INVENTION

There are various known processes for the synthesis of F32. The hydrogenolysis of F12 (dichlorodifluoromethane) or of F22 (patents JP 60-01731 and EP 508 660) has the disadvantage of being generally not very selective and of giving worthless methane as by-product. It has recently been proposed to produce F32 by fluorination of bis (fluoromethyl) ether (patent EP 518 506).

It is also possible to produce F32 by fluorination of methylene chloride (F30) using anhydrous HF. Many patents describe this reaction, claiming the use of catalysts such as $Cr_2O_3$, $CrF_3$, $AlF_3$, Cr/carbon, Ni/$AlF_3$ etc.

The difficulty in this reaction lies in the stability of the catalyst, which tends either to coke rapidly or to crystallize. The problem becomes very tricky if it is intended to combine a high space time yield and a good selectivity while maintaining good stability of the catalyst.

To reduce this deactivation it has been proposed to employ specific catalysts such as a mechanical mixture of alumina and chromium oxide (patent GB 821 211). This patent gives an example for the fluorination of methylene chloride, but the F32 space time yields obtained on this catalyst are low (<200 g/h/l) and the cumulative duration of the tests is shorter than 5 hours.

More generally, during fluorination reactions, it is very often envisaged to inject oxygen or air continuously to lengthen the lifetime of the catalysts. Thus, patent JP 51-82206 claims the use of 0.001 to 1% of oxygen to maintain the activity of a catalyst containing chiefly chromium oxide and optionally other metal oxides. It is indicated that the use of more than 1% of oxygen results in the appearance of secondary reactions and it is therefore recommended to employ preferably from 0.005 to 0.1% of oxygen. In this patent the fluorination reactions are carried out between 100 and 500° C. and preferably between 250 and 350° C. In addition, it is stated there that, starting at 200° C., the catalyst activity is maintained by the introduction of oxygen. Although this patent mentions, among the reactions, the fluorination of $CCl_4$, $CHCl_3$, $CH_2Cl_2$, $CCl_3F$, $C_2Cl_6$, $C_2Cl_4$ and $C_2H_3Cl_3$, the examples refer only to the fluorination of perhalogenated saturated materials ($CCl_4$ and $C_2Cl_3F_3$). It is known, however, that the reactivity of perhalogenated molecules is very different from that of the hydrogenated materials.

The latter, such as F133a (1-chloro-2,2,2-trifluoroethane) are sensitive to elimination reactions (loss of HCl or of HF) and to chlorination reactions, which result in the formation of worthless by-products. As patent FR 2 433 500 shows, the introduction of oxygen at the reaction temperature (generally higher than that employed for fluorinating perhalogenated molecules) can then result in a drop in selectivity.

Chromium oxide, well known as a fluorination catalyst, is also a good catalyst for the oxidation of HCl (U.S. Pat. No. 4,803,065 and U.S. Pat. No. 4,822,589). The oxygen introduced during the fluorination reaction reacts with the HCl formed to produce chlorine by the Deacon reaction. This chlorine can then easily cause a chlorination of the hydrogenated materials present in the reaction mixture. In the case of fluorination of F133a in the presence of oxygen, products of the F120 series ($C_2HCl_nF_{5-n}$) are thus chiefly formed. Besides the formation of chlorine, this Deacon reaction also produces water which, because of corrosion problems, is particularly undesirable in a fluorination process.

To overcome this disadvantage it has been proposed to employ some chromium-based mixed catalysts which make it possible to restrict the Deacon reaction. Thus, patent EP 546 883 shows that, in the case of bulk catalyst, the addition of a metal such as nickel allows the oxidation of HCl to be partially inhibited. A similar phenomenon is observed on Ni-Cr/$AlF_3$ mixed catalysts (patents EP 486 333 and WO 93/25507).

With a similar objective in view, patent EP 328 127 proposes to carry out the reaction of fluorination of F133a to F134a on a catalyst containing no chromium. The recommended solids contain at least one metal chosen from cobalt, manganese, nickel, palladium, silver, ruthenium and aluminium.

Recently, after having shown that in the case of the reaction of fluorination of methylene chloride in the presence of oxygen the chromium catalysts were not very selective (formation of F22 and of halogenated ethane derivatives), patent JP 5-339179 has also claimed the use of catalysts devoid of chromium, which are specific to the synthesis of F32. These catalysts, such as $CoCl_2$/$AlF_3$ or $NiCl_2$/$AlF_3$, are highly selective and their stability is increased by additives chosen from the rare earths (La, Ce) or alkaline-earth elements (Mg, Ca, Sr). The lifetimes obtained in the presence of oxygen are considerable (150 days), but the space time yields of F32 are very low (<10 g/h/l) and are not compatible with an industrial production of F32.

DESCRIPTION OF THE INVENTION

In trials of fluorination of methylene chloride, with a shorter contact time, aimed at increasing the space time yield of F32, we have been surprised to find that, in contrast to what the abovementioned patents lead one to expect, usual fluorination catalysts such as Ni/$AlF_3$ or Ni—Cr/$AlF_3$ are not stable, even in the presence of oxygen.

On the other hand, it has now been found that there is a temperature range in which a catalyst based on pure chromium (without the addition of another metal oxide) can produce, in the presence of oxygen, with an excellent stability, F32 by gas-phase fluorination of methylene chloride, without any significant loss of selectivity.

In fact, without an explanation being possible, it has first of all been surprising to find that the Deacon reaction is practically nonexistent, even when the methylene chloride fluorination reaction is carried out in the presence of large quantities of oxygen (3 mol %) between 250 and 450° C. on chromium oxide. The by-products originating from chlorination reactions are very minor in quantity. In addition, the absence of a Deacon reaction makes it possible to limit the generation of water in the reactor, and this limits the corrosion phenomena. The fluorination of methylene chloride is therefore a very special reaction, differing from the fluorination reactions such as those of F133a, $C_2Cl_4$, F123 or F124.

In contradiction to what might be expected from the prior art, it is therefore possible to employ a chromium-based catalyst to carry out this fluorination reaction in the presence of oxygen, without decrease in the selectivity of the reaction. It is therefore unnecessary to employ special additives in order to increase its selectivity; the elimination of the additives employed in the mixed catalysts enables the manufacture of the catalyst to be simplified and thereby its cost to be reduced.

The use of a chromium-based (bulk or supported) catalyst makes it possible furthermore to reach very high F32 space time yields. In addition, it has been surprising to find that, among the fluorination catalysts which have been tested, only the catalysts (bulk or supported) in which the active phase contains only chromium are capable of limiting coke formation at the temperature of fluorination of methylene chloride.

It has also been found that only a narrow temperature range enables the catalyst activity to be maintained efficaciously. Below 330° the introduction of oxygen does not enable the coke formation to be slowed down and the catalyst gradually becomes deactivated. On the other hand, the temperature which is higher than 400° C. can result in crystallization of the solid, entailing a decrease in its activity.

In summary, it has been found that, in order to prepare F32 in a high space time yield, in a stable and selective manner, it is necessary to combine an introduction of oxygen, a bulk or supported chromium-based catalyst and a restricted temperature range.

The subject of the invention is therefore a process for the manufacture of F32 by gas-phase catalytic fluorination of methylene chloride (F30) by means of anhydrous hydrofluoric acid, characterized in that the operation is carried out in the presence of 0.1 to 5 moles of oxygen per 100 moles of F30, at a temperature of between 330 and 450° C. and with a bulk or supported chromium catalyst.

The precursor employed for preparing the chromium catalyst according to the invention is preferably a chromium oxide, hydroxide, halide, acetate or nitrate. In the case of a solid catalyst a partially fluorinated, chromium-based solid with a large surface is preferably chosen, which may optionally contain inert components such as alumina or graphite in order to increase its thermal stability and its robustness. The catalyst may also be obtained by deposition of a chromium derivative on an inert support such as alumina or partially fluorinated alumina. The mass content of deposited chromium will then be preferably lower than 20%.

The oxygen may be introduced pure or diluted in an inert gas such as nitrogen. An $O_2/CH_2Cl_2$ molar ratio between 0.5 and 3% is preferably employed.

The $HF/CH_2Cl_2$ molar ratio may vary within wide limits. It is generally between 1.5 and 10, preferably between 2 and 5.

As indicated above, the reaction must be carried out at a temperature of between 330° C. and 450° C. However, it is preferable to work at a temperature of between 350 and 400° C., in order to obtain a high space time yield without risking deactivation of the catalyst due to crystallization.

The contact time, defined as the ratio of the total flow rate of the reactants (measured in the conditions of reaction) to the catalyst volume, may vary within wide limits and is generally between 0.01 and 10 seconds. In practice it is preferable to work with contact times of between 0.05 and 5 seconds.

The reaction may be carried out at atmospheric pressure or at a higher pressure. A pressure of between 1 and 20 bars absolute is preferably chosen.

EXAMPLES

The following examples illustrate the invention without limiting it.

CATALYST PREPARATION AND ACTIVATION

Bulk catalyst (A)

A bulk chromium oxide which has a specific surface of 209 $m^2/g$ and a pore volume (4 nm<r<63 $\mu$m) of 0.1 ml is employed after activation with anhydrous HF.

For this purpose the chromium oxide is first of all dried at 200° C. and then treated with an $N_2/HF$ mixture at 200° C. When the initial exothermicity has subsided, the temperature is raised to 380° C. The catalyst is then kept at 380° C. for 18 hours under a stream of pure anhydrous HF.

The activated catalyst (A) has the following physicochemical properties:

Fluorine weight content: 27%

Chromium weight content: 53%

Volume of the pores with a radius of between 4 nm and 63 $\mu$m: 0.13 ml/g

BET surface: 101 $m^2/g$

Supported catalysts (B), (C) and (D)

In a rotary evaporator are placed 250 ml of partially fluorinated alumina (containing, in all, 83 mass % of aluminium fluoride and 16% of alumina), obtained beforehand by the fluorination of alumina at about 300° C. with the aid of nitrogen and hydrofluoric acid. This fluorinated support has the following physicochemical characteristics before impregnation:

form: beads 1–2 mm in diameter apparent density: 0.57 g/ml

BET surface: 67 $m^2/g$ pore volume: 0.72 ml/g (in the case of pores with a radius of between 4 nm and 63 $\mu$m).

An aqueous solution (solution 1) containing the desired metal precursors is prepared separately, using the quantities shown in Table 1. In the case of the catalysts (B) and (D), which are prepared from $CrO_3$, the impregnation is carried out in a methanolic medium, so as to reduce the chromium to the oxidation state III. To do this, the aqueous solution containing the chromium and a methanolic solution (solution 2) are added simultaneously onto the support, with stirring.

TABLE I

| | Solution 1 | Solution 2 |
|---|---|---|
| Catalyst B | $CrO_3$ = 32.5 g | $CH_3OH$ = 46 g |
| | $H_2O$ = 70 g | $H_2O$ = 15 g |
| Catalyst C | 20 g $NiCl_2.6H_2O$ | none |
| | $H_2O$ = 95 g | |
| Catalyst D | $CrO_3$ = 12.5 g | $CH_3OH$ = 17.8 g |
| | $NiCl_2.6H_2O$ = 29 g | $H_2O$ = 50 g |
| | $H_2O$ = 40 g | |

The impregnation is carried out over 45 minutes, at ambient temperature and atmospheric pressure, on the support which is being stirred. The catalyst is then dried for 4 hours under a nitrogen stream, in a fluidized bed, at about 110° C.

The catalyst is then charged into a reactor made of Inconel 600 and activated in a stationary bed with a nitrogen/HF mixture in accordance with the procedure described in patent EP 0 486 333. Table II, which follows, shows the chemical composition of the catalysts thus activated.

TABLE II

| Catalyst | Chemical composition (by weight) |
|---|---|
| B | Cr = 12%; F = 56%; Al = 25% |
| C | Ni = 3%; F = 66%; Al = 30% |
| D | Cr = 6%; Ni = 6%; F = 57%; Al = 26% |

FLUORINATION OF METHYLENE CHLORIDE

Example 1

4 ml of prefluorinated chromium oxide (catalyst A) are charged into a tubular reactor made of Inconel 600, with an internal diameter of 1 cm and a volume of 40 ml. In a first stage, HF and air are introduced at respective flow rates of 0.68 mol/h and 0.03 mol/h. Methylene chloride, vaporized in a preheater, the temperature of which is set at 150° C., is introduced next in gaseous form into the reactor at a flow rate of 0.23 mol/h. The reaction is carried out at atmospheric pressure. The reactor temperature is maintained at 350° C. and the contact time in these conditions is 0.3 seconds.

The reaction products are then washed, dried and analysed by gas chromatography. The results are brought together in Table III which follows.

TABLE III

| Time (h) | F30 conversion (mol %) | F31 selectivity (mol %) | F32 selectivity (mol %) |
|---|---|---|---|
| 24 | 64 | 27 | 73 |
| 151 | 60 | 28 | 72 |
| 201 | 62 | 27 | 73 |
| 314 | 63 | 27 | 73 |
| 428 | 61 | 27 | 73 |
| 524 | 63 | 27 | 73 |
| 640 | 62 | 28 | 72 |
| 893 | 60 | 27 | 73 |
| 971 | 61 | 27 | 73 |

Measurement of the $O_2/N_2$ ratio makes it possible, furthermore, to verify whether the oxygen introduced in the form of air has been consumed. In these reaction conditions 5% of the oxygen introduced is converted to CO; $CO_2$ formation is marginal. Other by-products (F23 and F40) are in quantities that are smaller than 700 ppm. The $O_2/N_2$ molar ratio at the reactor exit is 0.26, which shows the absence of the Deacon reaction.

It is found that these reaction conditions enable a completely stable activity to be maintained with the very high space time yield of F32 (1350 g/h/l) and a selectivity for F31+F32 higher than 99.7%.

Comparative Example 1

The reaction is carried out in the same conditions as Example 1 but at a temperature of 300° C. The flow rate of the reactants is adjusted so as to maintain a contact time of 0.3 seconds. The results are brought together in the following table.

TABLE IV

| Time (h) | F30 conversion (mol %) | F31 selectivity (mol %) | F32 selectivity (mol %) |
|---|---|---|---|
| 24 | 54 | 24 | 76 |
| 96 | 42 | 27 | 73 |
| 220 | 40 | 31 | 69 |
| 321 | 33 | 34 | 66 |

The oxygen introduced takes practically no part in the reaction; the quantity of $CO/CO_2$ formed is smaller than the detection threshold (<0.05%).

The catalyst has become deactivated by coking and after 321 hours' running contains 2.5% (mass) of carbon.

It is found that a temperature of 300° C. does not allow a stable activity to be maintained on this catalyst. This temperature enables a high F32 space time yield to be obtained (1200 g/h/l) but is insufficient in order continuously to suppress the formation of coke or of its precursors.

Example 2

The methylene chloride fluorination reaction is carried out in the same conditions as in Example 1 on the supported catalyst B (Cr/AlF$_3$). The results obtained are brought together in Table V.

TABLE V

| Time (h) | F30 conversion (mol %) | F31 selectivity (mol %) | F32 selectivity (mol %) |
|---|---|---|---|
| 90 | 57.6 | 29.4 | 70.6 |
| 226 | 55.7 | 30.5 | 69.4 |
| 274 | 53.7 | 32.9 | 67.0 |
| 372 | 55.9 | 30.8 | 69.1 |
| 493 | 54.9 | 31.6 | 68.2 |
| 564 | 53.7 | 32.1 | 67.8 |

The oxygen introduced takes very little part in the reaction; the quantity of $CO/CO_2$ formed is smaller than the detection threshold (<0.05%). The formation of 100 ppm of bis(fluoromethyl) ether is observed.

Comparative Examples 2 and 3

The reaction is carried out in the conditions of Example 1 on supported catalysts C and D (Ni/AlF$_3$ and Ni-Cr/AlF$_3$) which are not in accordance with the present invention.

The methylene chloride conversion and the selectivities for F32 and F31 are shown in Table VI which follows:

TABLE VI

| Comparative Example | Time (h) | F30 conversion (mol %) | F31 selectivity (mol %) | F32 selectivity (mol %) |
|---|---|---|---|---|
| 2 (Catalyst C) | 23 | 53.6 | 31.5 | 67.3 |
|  | 47 | 44.3 | 38.6 | 61.4 |
|  | 71 | 39.7 | 42.3 | 57.7 |
|  | 95 | 37.4 | 44.0 | 56.0 |

Carbon content of the spent catalyst: 1.7 mass %

| | | | | |
|---|---|---|---|---|
| 3 (Catalyst D) | 48 | 64 | 26 | 74 |
|  | 144 | 57 | 30 | 70 |
|  | 290 | 48 | 35 | 65 |

Carbon content of the spent catalyst: 2 mass %

It is found that fluorination catalysts C and D do not make it possible to attain the lifetime obtained on catalysts A and B which are based on chromium alone (solid or supported) and are deactivated by coking despite the continuous introduction of air and the high temperature.

Less than 500 ppm of $CO/CO_2$ is formed on these catalysts, and no bis(fluoromethyl) ether (<10 ppm) is formed. The oxygen introduced does not react.

These Comparative Examples 2 and 3 show that it is necessary to have a catalyst containing solely chromium (catalysts A and B) in order that the air introduced may suppress or inhibit coke formation at the temperature of fluorination of methylene chloride. Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. Process for the manufacture of difluoromethane consisting essentially of gas-phase catalytic fluorination of methylene chloride with anhydrous hydrofluoric acids in the presence of 0.1 to 5 moles of oxygen per 100 moles of methylene chloride, at a temperature of between 330 and 450° C. and with a bulk or supported chromium catalyst.

2. Process according to claim 1, wherein the $O_2/CH_2Cl_2$ molar ratio is between 0.5% and 3%.

3. Process according to claim 1 wherein the operation is carried out at a temperature of between 350 and 400° C.

4. Process according to claim 1 wherein a bulk chromium catalyst is employed.

5. Process according to claim 1 wherein a supported chromium catalyst is employed, the weight content of chromium being less than 20%.

6. Process according to claim 1 wherein the gas phase mixture of methylene chloride, anhydrous hydrogen fluoride and oxygen is in contact with the catalyst for a time between 0.01 and 10 seconds.

7. Process according to claim 1 wherein the process is carried out at a pressure of between 1 and 20 bars absolute.

8. Process according to claim 6, wherein the time of contact is between 0.05 and 5 seconds.

9. Process for the manufacture of difluoromethane consisting of gas-phase catalytic fluorination of methylene chloride with anhydrous hydrofluoric acid in the presence of 0.1 to 5 moles of oxygen per 100 moles of methylene chloride, at a temperature of between 330 and 450° C. and with a bulk or supported chromium catalyst.

10. Process for the manufacture of difluoromethane consisting essentially of gas-phase catalytic fluorination of methylene chloride with anhydrous hydrofluoric acid in the presence of 0.1 to 5 moles of oxygen per 100 moles of methylene chloride, at a temperature from greater between 330° to 450° C. and with a bulk or supported chromium catalyst, the gas phase mixture of methylene chloride, anhydrous hydrogen fluoride and oxygen is in contact with the catalyst for a time between 0.01 and 10 seconds.

* * * * *